United States Patent [19]

Kaulen

[11] Patent Number: 4,720,558

[45] Date of Patent: Jan. 19, 1988

[54] PROCESS FOR INVERTING THE CONFIGURATION OF SECONDARY ALCOHOLS

[75] Inventor: Johannes Kaulen, Leverkusen, Fed. Rep. of Germany

[73] Assignee: Bayer Aktiengesellschaft, Leverkusen, Fed. Rep. of Germany

[21] Appl. No.: 838,745

[22] Filed: Mar. 11, 1986

[30] Foreign Application Priority Data

Mar. 28, 1985 [DE] Fed. Rep. of Germany ....... 3511210

[51] Int. Cl.$^4$ .................. C07D 317/54; C07C 31/135; C07C 31/125
[52] U.S. Cl. .................................. 549/443; 549/444; 568/906; 568/904; 568/886; 568/834; 568/832; 568/823; 568/7.5; 260/397.2; 260/397.25
[58] Field of Search ............... 568/906, 902, 834, 832, 568/886, 715, 823; 549/437, 438, 443, 444; 260/397.2, 397.25

[56] References Cited

PUBLICATIONS

Synthesis 1981, pp. 1–3.
Ann. Chem. 1974, 821.
Journal of the American Chemical Society, 96, 5876, 1974.
J. Org. Chem. 1981, 46, 4321–4323.
Tetrahedron Letters No. 32, pp. 3265–3268, 1972.
Tetrahedron Letters No. 37, pp. 3183–3186, 1975.
Synthesis 1980, pp. 292–295.
Synthesis 1979, pp. 561–565.
Angew. Chem. 78, 483 (1966).
J. March, Advanced Organic Chemistry, 2, pp. 276–279.

Primary Examiner—Nicky Chan
Attorney, Agent, or Firm—Sprung Horn Kramer & Woods

[57] ABSTRACT

Process for inverting the configuration of secondary alcohols in which the hydroxyl group is attached to an asymmetric carbon atom, in accordance with which the secondary alcohols are esterified, with inversion of their configuration, by conversion into isourea ethers and reaction of these isourea ethers with carboxylic acids, and the esters are then saponified with retention of the configuration of the secondary alcohols.

4 Claims, No Drawings

PROCESS FOR INVERTING THE CONFIGURATION OF SECONDARY ALCOHOLS

The present invention relates to a new process for inverting the configuration of secondary alcohols in which the hydroxyl group is attached to an asymmetric carbon atom.

Processes for inverting the configuration of secondary alcohols are already known. They are based on esterifying, with inversion of their configuration, secondary alcohols in which the hydroxyl function is attached to an asymmetric carbon atom, with carboxylic acids in the presence of azodicarboxylic acid ester/triphenylphosphine (Synthesis 1981, 1) or of neopentyl acetals of dimethylformamide (Ann. Chem. 1974, 821), and saponifying the esters with retention of their configuration. In other processes the secondary alcohol is first converted into a methanesulphonic or p-toluenesulphonic acid ester, which is then inverted by means of sodium, caesium or ammonium salts of carboxylic acids (see J. Am. Chem. Soc. 96, 5786 (1974); J. Org. Chem. 46, 4321 (1981); or Tetrahedr. Lett. 1972, 3265), by means of potassium peroxide in the presence of crown ethers (Tetrahedr. Lett. 1975, 3183) or by means of potassium nitrite in dimethyl sulphoxide (Synthesis 1980, 292), and is then saponified to give the alcohol having the inverted configuration. However, these known processes exhibit considerable disadvantages: thus, for example, they require the use of expensive auxiliary reagents; the removal of the auxiliary reagents and/or the working up of the esterification mixtures is difficult, particularly if it is necessary to use solvents which are difficult to remove, such as dimethyl sulphoxide or dimethylformamide; as a result of the formation of by-products (olefines), the yields vary considerably. The processes proceeding via the methanesulphonic and p-toluenesulphonic acid esters have the additional disadvantage that they require two separate reaction stages.

It has now been found, surprisingly, that inversion takes place when isourea ethers of secondary alcohols in which the hydroxyl group is attached to an asymmetric carbon atom, are reacted with carboxylic acids to give esters of these secondary alcohols. That is to say, the esters prepared from the isourea ethers and the alcohols obtained from the latter have the opposite configuration to the starting alcohol at the asymmetric carbon atom. Since isourea ethers of secondary alcohols are readily accessible, the discovery that the esterification of the secondary alcohols via the isourea ethers takes place with inversion of the configuration of the secondary alcohol opens up a new, simple, economical process for inverting the configuration of secondary alcohols.

The invention therefore relates to a new process for inverting the configuration of secondary alcohols in which the hydroxyl function is attached to an asymmetric carbon atom by esterifying these secondary alcohols, with inversion of their configuration, and subsequent saponification of the esters with retention of the configuration of the secondary alcohol, which process is characterized in that the esterification with inversion of the configuration of the secondary alcohol is carried out by first converting the secondary alcohol into an isourea ether, and reacting this isourea ether with a carboxylic acid to give the ester of the secondary alcohol.

The process according to the invention may be illustrated by means of the following reaction diagram:

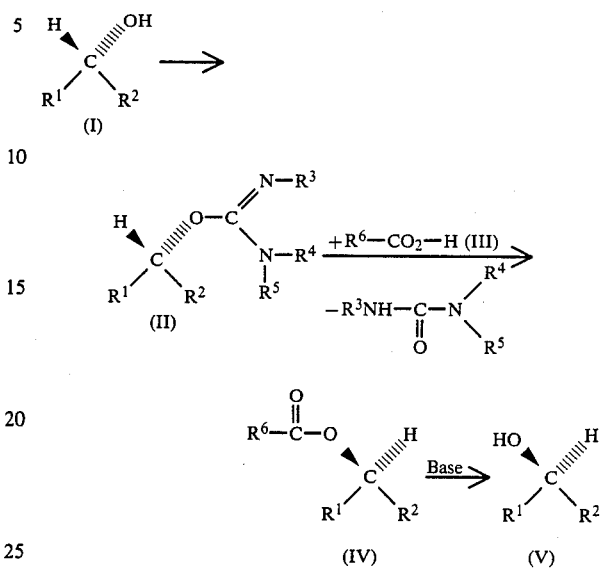

Admittedly, it is already known that alcohols can be esterified by converting them into an isourea ether, for example by an addition reaction with a carbodiimide, and reacting this isourea ether with a carboxylic acid (see Synthesis 1979, 561; and Angew. Chem. 78, 483 (1966)). Hitherto, however, nothing has been known about the stereochemical pattern of this esterification in the case of secondary alcohols. It must be regarded as extremely surprising that, in accordance with the process according to the invention, the inverted esters, and with them also the secondary alcohols having the inverted configuration, are obtained not only in a high yield, but also in an extremely high degree of optical purity (or purity of diastereomers), since it would have been expected that racemization would take place, at least partially, in the reaction of the isourea ethers to give the carboxylic acid esters.

In the secondary alcohols of the formula

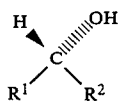

(I)

$R^1$ and $R^2$ independently of one another represent an optionally substituted, saturated or unsaturated, aliphatic or cycloaliphatic hydrocarbon radical or an optionally substituted araliphatic or aromatic hydrocarbon radical, or together form an asymmetric alkylene radical, subject to the proviso that $R^1$ is not the same as $R^2$. The nature of the radicals $R^1$ and $R^2$ is not significant for the stereochemical pattern of the esterification reaction; the only decisive factor is that the central carbon atom carrying the OH group is a centre of asymmetry, that is to say that the radicals $R^1$ and $R^2$ are different.

The conversion of the alcohols of the formula (I) into the isourea ethers of the formula

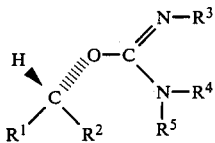 (II)

in which
R³, R⁴ and R⁵ independently of one another represent an optionally substituted alkyl, cycloalkyl, aralkyl or aryl radical and
R⁵, in addition to these radicals, can also additionally be hydrogen,
is preferably effected by an addition reaction of the secondary alcohols of the formula (I) with carbodiimides of the formula

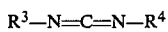 (VI)

in which $R^3$ and $R^4$ have the meaning indicated under formula (II).

The isourea ethers of the formula (II) are converted, with inversion of the alcohol configuration, by reaction with carboxylic acids of the formula

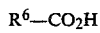 (III)

in which $R^6$ represents hydrogen or an optionally substituted, saturated or unsaturated, aliphatic or cycloaliphatic hydrocarbon radical or an optionally substituted araliphatic or aromatic hydrocarbon radical, into esters of the formula

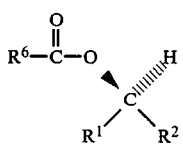 (IV)

in which $R^1$, $R^2$ and $R^6$ have the meaning indicated under the formulae (I) and (III).

If the carbon atom to which the hydroxyl group is attached is the only centre of asymmetry in the molecule, the S-enantiomer (R-enantiomer) of the secondary alcohol of the formula (I) is obtained, in accordance with the process according to the invention, from the R-form (S-form) in a high state of optical purity.

If, however, in addition to the carbon atom carrying the hydroxyl group, the molecule also contains one or more further centres of asymmetry, the diastereomers of this secondary alcohol of the formula (I) are obtained in a high state of diastereomer purity.

Saturated, aliphatic hydrocarbon radicals which may be mentioned for $R^1$, $R^2$ and $R^6$ are $C_1$–$C_{12}$-alkyl radicals, such as the methyl, ethyl, n-propyl, iso-propyl, n-butyl, iso-butyl, tert.-butyl, n-pentyl, 2-methylpentyl, n-hexyl, i-hexyl, 2-ethyl-hexyl and n-dodecyl radical; unsaturated, aliphatic hydrocarbon radicals which may be mentioned are $C_1$–$C_8$-alkenyl radicals, such as the allyl and the 2-hexenyl radical, and alkenyl radicals, such as the propargyl radical. Suitable saturated, cycloaliphatic hydrocarbon radicals are, above all, cycloalkyl radicals, such as the cyclopropyl, cyclobutyl, cyclopentyl, cyclohexyl and the cycloheptyl radical. The cyclohexenyl radical, above all, may be mentioned as an unsaturated, cycloaliphatic hydrocarbon radical.

Suitable aromatic hydrocarbon radicals are, above all, the phenyl and the naphthyl radical, while suitable araliphatic hydrocarbon radicals are aralkyl radicals, such as the benzyl, β-phenylethyl, γ-phenylpropyl and ω-phenylbutyl radical. Substituted ethylene radicals, such as the 1,2-propylene radical and also the 1,3-butylene radical and asymmetrically substituted 1,5-pentylene and 1,6-hexylene radicals may, above all, be mentioned as aSymmetric alkylene radicals which together can form $R^1$ and $R^2$. Further rings can be fused to the alkylene radicals, as is the case, for example, in the compounds derived from cholestane.

The radicals mentioned above for $R^1$, $R^2$ and $R^6$ can optionally be substituted by halogen, alkyl, alkoxy, nitrile, formyl, alkylcarbonyl, alkoxycarbonyl, aminocarbonyl or dialkylaminocarbonyl groups.

The following may be mentioned as examples of alkyl radicals for $R^3$, $R^4$ and $R^5$: $C_1$–$C_8$-alkyl radicals, such as the methyl, ethyl, n-propyl, iso-propyl, n-butyl, iso-butyl, tert.-butyl, n-pentyl, 2-methylpentyl, 3-methylpentyl, n-hexyl, i-hexyl and 2-ethylhexyl radical; as cycloalkyl radicals: cyclopropyl, cyclobutyl, cyclopentyl, cyclohexyl, cycloheptyl or cyclooctyl radicals; as aralkyl radicals: in particular the benzyl and 2-phenylethyl radical; and as aryl radicals, in particular the phenyl or naphthyl radical. The aralkyl and aryl radicals can be substituted by halogen or by lower alkyl or lower alkoxy groups.

The nature of the radicals $R^3$, $R^4$, $R^5$ and $R^6$ is not significant for the pattern of the inversion reaction according to the invention. For reasons of cost the carbodiimides (VI) and carboxylic acids (III) used will be as simple as possible and hence cheaply accessible; examples of carbodiimides used are dicyclohexylcarbodiimide or diisopropylcarbodiimide, and examples of carboxylic acids used are formic, acetic, benzoic, acrylic or methacrylic acid.

The addition reaction between the secondary alcohols of the formula (I) and the carbodiimides of the formula (VI) can be carried out in accordance with known processes (see Synthesis 1979, 561; and Angew. Chem. 78, 483 (1966)) in the manner described therein, by reacting the alcohols of the formula (I), in the presence of Lewis acids and, if appropriate, in an organic solvent, with the carbodiimides of the formula (VI) to give the isourea ethers of the formula (II).

Examples of suitable Lewis acids for the addition reaction are copper(I) and copper(II) halides, titanium-(IV) halides, titanium(IV) alcoholates and zinc, tin, iron or boron halides; it is preferable to employ copper(I) or copper(II) chloride. The Lewis acids are added in amounts of 0.01 to 5 mol %, preferably 0.1 to 1 mol %.

The addition reaction between the secondary alcohols and the carbodiimides can be carried out in the absence of solvents, but it is also possible to use aprotic organic solvents, such as hydrocarbons, ethers, acid amides or nitriles. In the event that the addition reaction is carried out in a solvent, it is preferable to select for this reaction the same solvent as that used in the subsequent reaction of the isourea ethers with the carboxylic acids.

The reaction of the secondary alcohols with the carbodiimides is carried out at temperatures from 0° to 200° C., preferably 20° to 100° C., and, if appropriate, in an inert gas atmosphere. In the reaction of the secondary alcohols with the carbodiimides the alcohol and the carbodiimide are employed in molar ratios of 1:1 to 1:1.5, preferably 1:1 to 1:1.1. In general, the isourea ethers (II) are not isolated, but are immediately reacted with the carboxylic acids in the form in which they are obtained after the reaction of the secondary alcohols with the carbodiimides. In principle, however, it is possible to isolate the isourea ethers by distillation or crystallization.

The isourea ethers of the formula (II) are then reacted with the carboxylic acids (III), with inversion of the configuration of the alcohol, to give the esters (IV). This reaction is carried out by dissolving the isourea ethers in an aprotic solvent and adding 1 to 1.5, preferably 1 to 1.1, equivalents of carboxylic acid at temperatures from 0° to 150°, preferably 10° to 50° C., and reacting the mixture at temperatures from 20° to 200° C., preferably at the boiling point of the solvent used. The reaction time is 2 to 24 hours, depending on the size of the batch and the reactivity of the isourea ether used.

During the reaction, the substituted urea formed from the isourea ether is precipitated. It can be removed in a simple manner, for example by filtration.

The aprotic organic solvents used for the esterification reaction are preferably aliphatic or aromatic hydrocarbons, such as petroleum ether, cyclohexane, benzene or toluene; or ethers, such as diethyl ether, tetrahydrofuran or dioxane; acid amides, such as dimethylformamide or nitriles, such as acetonitrile, can also be employed. It is preferable, however, to employ toluene or dioxane. The reaction solutions available after the reaction are freed from the solvent in a customary manner. The esters of the formula (IV), which are left as a residue, can be saponified immediately without further purification, or are first purified by distillation, crystallization or column chromatography and are then saponified.

The saponification of esters of the formula (IV), with retention of the configuration, to give the secondary alcohols (V) is a known reaction of organic chemistry. It is usually carried out by reacting the ester (IV) with alkali metal or alkaline earth metal hydroxides or with alkali metal alcoholates. The saponification is preferably carried out by stirring the ester (IV) with 0.1 to 10 mol %, preferably 1 to 5 mol %, of sodium methoxide in methanol at room temperature. The secondary alcohol having an inverted configuration is then isolated from the saponification mixture by distillation.

If the secondary alcohol of the formula (I) which is used as the starting compound has the R-configuration at the carbon atom carrying the hydroxyl group, the ester (III) obtained by the process according to the invention and the secondary alcohol of the formula (V) obtained from the latter have the S-configuration, and conversely.

The process according to the invention may be illustrated using (−)-menthol as an example:

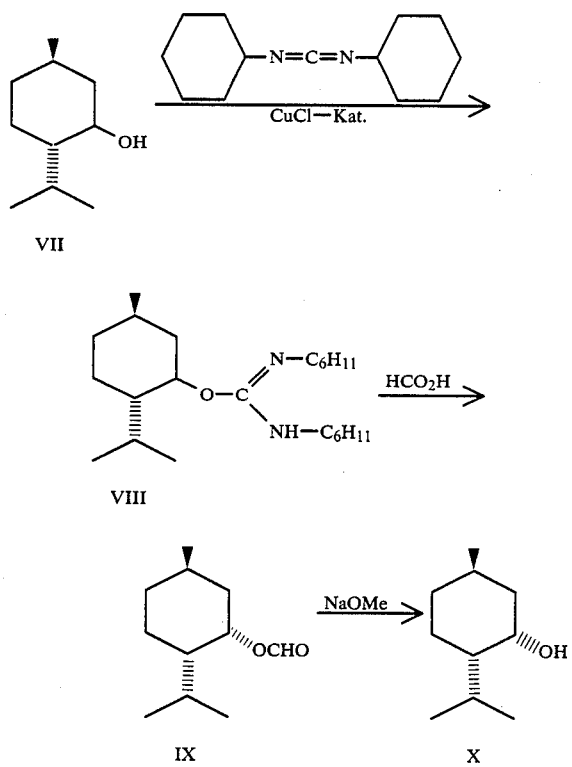

Optically pure (−)-menthol (VII) (R-configuration at the carbon atom carrying the hydroxyl group) is subjected to an addition reaction in the manner illustrated above with dicyclohexylcarbodiimide. The resulting isourea ether (VIII) is immediately, that is to say without intermediate purification, reacted with formic acid. Neomenthyl formate (IX) (S-configuration at the carbon atom carrying the ester group; enantiomeric excess > 99%) is obtained in a high yield, with inversion of configuration. Neomenthol (X), which differs from (−)-menthol (VII) in having the S-configuration at the carbon atom carrying the hydroxyl group, is obtained from this ester by saponification (enantiomeric excess > 99%).

The secondary alcohols indicated in Table 1 below were inverted analogously to (−)-menthol in the yield also indicated in the table and in the enantiomeric excess indicated in the table.

TABLE 1

| Secondary alcohol (I) | Configuration at C—OH | Carboxylic acid (III) | Inverted ester (IV) | | | Inverted alcohol (V) | | |
|---|---|---|---|---|---|---|---|---|
| | | | Yield[a] | e.e.[a] | Configuration | Yield | e.e.[a] | Configuration |
| CH₃–(CH(OH))–CH₃ (with chain) | S | CH₃COOH | 66% | >99% | R | 90% | 99% | R |
| | | HCOOH | 83% | >99% | R | | | |
| (±) cyclohexyl-OH, CH₃ | R,S | HCOOH | 50% | >99%[b] | S,R | 91% | 99%[b] | S,R |

TABLE 1-continued

| Secondary alcohol (I) | Configuration at C—OH | Carboxylic acid (III) | Inverted ester (IV) Yield[a] | Inverted ester (IV) e.e.[a] | Inverted ester (IV) Configuration | Inverted alcohol (V) Yield | Inverted alcohol (V) e.e.[a] | Inverted alcohol (V) Configuration |
|---|---|---|---|---|---|---|---|---|
| (menthol structure with OH) | R | HCOOH | 80% | >99% | S | | | |
| | R | $CH_2=CH-COOH$ | 51% | >99% | S | 90% | 99% | S |
| | R | $CH_2=C(CH_3)-COOH$ | 64% | >99% | S | | | |
| (cholesterol structure HO-) | S | HCOOH | >75% | >99% | R | 90% | >99% | R |
| (structure XI with OH, CH₃, methylenedioxyphenyl) | S:R 79:21 | HCOOH | 84% | — | — | 89% | S:R = 31:69 | XII |

Compared with the known processes, the process according to the invention has the following important advantages, which also render the process of interest for application on an industrial scale:

The process according to the invention takes place with high yields and an excellent stereoselectivity; the reaction takes place under mild, clearly neutral conditions, so that it is also applicable to the inversion of the configuration of secondary alcohols containing sensitive functional groups; the reaction can be carried out in a single stage, since the isourea ethers formed as intermediates do not have to be isolated, but can be reacted immediately with the carboxylic acids; working up the reaction mixture produced in the formation of the esters and removal of the auxiliary reagent (substituted urea) is particularly simple, since the substituted ureas formed in addition to the esters from the isoureas are precipitated under the reaction conditions and can be removed directly by mechanical means, for example by filtration; in addition, the carbodiimides and carboxylic acids required as auxiliary reagents are technically easily accessible and are therefore moderately priced. In very general terms, the process according to the invention is useful for obtaining, from readily accessible stereoisomers, stereoisomers of secondary alcohols or esters thereof which are difficult of access. Compounds of this type, particularly those in the form of pure enantiomers, are of interest as intermediate products, for example for active compounds in pharmacy or in agriculture, since, as is known, stereoisomers often differ considerably in their activity.

It can be advantageous to obtain an enantiomer of a secondary alcohol by inversion of its optical antipode, if, for example, only the optical antipode is accessible as a natural substance or if only the antipode can be obtained in a simple manner by microbiological reduction. The process according to the invention can also be used with success to recover the undesired enantiomer subsequent to resolving the racemate of a secondary alcohol, that is to say to convert it also into the desired stereoisomer by inversion. The process according to the invention is also of great interest for obtaining esters capable of polymerization in a simple manner, for example acrylates or methacrylates, of optically active secondary alcohols, in the form of the pure enantiomers, which can be polymerized to give optically active polymers.

The process according to the invention may be illustrated by means of the following examples.

EXAMPLE 1

(a) Esterification with inversion of configuration 156 g (1 mole) of (—)-menthol ($[\alpha]_D^{20} = -48.5°$ (c=5, EtOH)) are stirred with 248 g (1.2 moles) of dicyclohexylcarbodiimide and 100 mg of copper(I) chloride for 3 days at room temperature. The reaction mixture is taken up in 400 ml of dry toluene, 45 ml (1.2 moles) of concentrated formic acid are added to the solution, and the mixture is stirred for 20 hours at 110° C.

The precipitated dicyclohexylurea is filtered off and washed with methylene chloride. The organic filtrate is freed from the solvent in vacuo. The residue is taken up in ether. The ether solution is washed with sodium bicarbonate solution until it is neutral, and is then dried over sodium sulphate and subsequently freed from the solvent in vacuo. The residue is distilled.

147 g (80% of theory) of neomenthyl formate are obtained. Boiling point: 52°-60° C./0.25 mbar; $[\alpha]_D^{20} = +51.9°$ (undiluted); enantiomeric excess >99%.

(b) Saponification

A mixture of 122.5 g (0.67 mole) of neomenthyl formate, 6 ml of 30% strength sodium methoxide solution and 250 ml of methanol is stirred for 12 hours at room temperature. After the methanol has been removed by distillation, the residue is distilled in vacuo.

93.4 g (90% of theory) of neomenthol are obtained (boiling point: 94°-98° C./18 mbar; $[\alpha]_D^{20} = +19.6°$ (c=1, EtOH); menthol content according to capillary gas chromatography <0.2%; enantiomeric excess >99%.

EXAMPLE 2

61.8 g (0.4 mole) of (—)-menthol are stirred with 50 g (0.4 mole) of diisopropylcarbodiimide and 50 mg of copper(I) chloride for 3 days at room temperature. The isourea ether formed is isolated by distillation.

101 g (90% of theory) of 0-(—)-menthyl-N,N'-diisopropyl-isourea ether are obtained; boiling point: 80°-90° C./0.03 mbar.

The 101 g of isourea ether are reacted with 16 ml of formic acid in 200 ml of dry toluene as described in Example 1(a).

54.5 g (83% of theory) of neomenthyl formate are obtained.

EXAMPLE 3

The isourea ether prepared in accordance with Example 1(a) from 156 g (1 mole) of (−)-menthol and 248 g (1.2 moles) of dicyclohexylcarbodiimide is stirred with 82 ml (1.2 moles) of acrylic acid in 400 ml of dry toluene for 20 hours at 110° C. The mixture of esters is worked up as described in Example 1a). Distillation gives 106 g (51% of theory) of neomenthyl acrylate; boiling point: 60°–65° C./0.1 mbar; $[\alpha]_D^{20} = +47.1$ (c=1, EtOH).

A sample of the neomenthyl acrylate saponified in accordance with Example 1(b) to prove its configuration contained, according to capillary gas chromatography, only <1% of menthol in addition to neomenthol (enantiomeric excess 99%).

If 102 ml (1.2 moles) of methacrylic acid are used instead of the 1.2 moles of acrylic acid, 143 g (64% of theory) of neomenthyl methacrylate are obtained; boiling point: 65°–72° C./0.1 mbar. The optical purity of the neomenthyl methacrylate is comparable with the optical purity of the neomenthyl acrylate.

EXAMPLE 4

The isourea ether obtained in the manner described in Example 1a) from 6.5 g (50 mmol) of (S)-2-octanol ($[\alpha]_D^{20} = +9.59°$, undiluted) and 12.4 g (60 mmol) of dicyclohexylcarbodiimide is stirred, in 30 ml of anhydrous dioxane, with 2.76 g (60 mmol) of anhydrous formic acid for 20 hours at 100° C. The reaction mixture is worked up as described in Example 1a).

Distillation gives 6.55 g (83% of theory) of (R)-2-formyloxy-octane; boiling point: 35° C./0.04 mbar; $[\alpha]_D^{20} = +3.75°$ (undiluted); enantiomeric excess >99%.

Saponification of the ester in the manner described in Example 1b) with 0.15 ml of 30% strength sodium methoxide solution in 10 ml of methanol gives 4.69 g (90% of theory) of (R)-2-octanol; boiling point: 50°/0.1 mbar; $[\alpha]_D^{20} = -9.36°$ (undiluted); enantiomeric excess >99%.

EXAMPLE 5

The process is carried out as described in Example 4, but 3.6 g (60 mmol) of glacial acetic acid are used instead of the formic acid, and the reaction mixture is stirred for 8 hours at 100° C.

5.71 g (66% of theory) of (R)-2-acetoxyoctane are obtained; boiling point: 70°–75° C./0.5 mbar; $[\alpha]_D^{20} = -6.32°$ (undiluted); enantiomeric excess >99%.

Saponification of the (R)-2-acetoxyoctane to give (R)-2-octanol is carried out as described for the formate in Example 4.

EXAMPLE 6

The isourea ether prepared in accordance with Example 1(a) from 20 g (0.175 mole) of (±)trans-2-methylcyclohexanol and 43.3 g (0.21 mole) of dicyclohexylcarbodiimide is reacted with 7.9 ml (0.21 mole) of anhydrous formic acid and 80 ml of anhydrous toluene for 20 hours at reflux temperature. The esterification mixture is worked up as described in Example 1.

12.4 g (50% of theory) of (±)cis-1-formyloxy-2-methylcyclohexane are obtained; boiling point: 65°–70° C./16 mbar.

Saponification of 5 g (35 mmol) of this (±)cis-1-formyloxy-2-methylcyclohexane with 0.3 ml of 30% strength sodium methoxide solution in 15 ml of methanol in accordance with Example 1b) gives 3.66 g (91% of theory) of (±)cis -2-methylcyclohexanol; boiling point: 75° C. /18 mbar; according to capillary gas chromatography, the cis-proportion is >98% and the trans-proportion is <1%; the diastereomeric excess is >99%.

EXAMPLE 7

19.4 g (50 mmol) of dihydrocholesterol are stirred with 12.4 g (60 mmol) of dicyclohexylcarbodiimide and 20 mg of copper(I) chloride in 30 ml of anhydrous dioxane for 3 days at 60° C. 2.80 g (60 mmol) of anhydrous formic acid are then added to the reaction mixture. The esterification mixture is stirred for 20 hours at 100° C. and is then worked up as described in Example 1a).

20.8 g (100% of theory) of crude, but already very pure, 3α-formyloxy-5α-cholestane are obtained; melting point: 107°–108° C.

Purification by column chromatography over silica gel (mobile phase: 10:1 petroleum ether/ether) gives 14.4 g (=75% of theory) of pure 3α-formyloxy-5α-cholestane; $[\alpha]_D^{20} = +29.5°$ (c=1, CHCl₃); enantiomeric excess >99%.

Saponification of 7.0 g (16.8 mmol) of the crude product with 0.1 ml of 30% strength sodium methoxide solution in the manner described in Example 1b) gives 6.30 g (=97% of theory) of 3α-hydroxy-5α-cholestane. The compound is purified by chromatography over silica gel (mobile phase: 95:5 methylene chloride/methanol). 5.84 g (=90% of theory) of pure 3αhydroxy-5α-cholestane are obtained; melting point: 177°–179° C.

EXAMPLE 8

The isourea ether prepared in accordance with Example 1(a) from 9.7 g (50 mmol) of the alcohol XI (S:R enantiomer ratio=79:21) and 11.4 g (55 mmol) of dicyclohexylcarbodiimide is stirred with 2.3 g (50 mmol) of anhydrous formic acid in 20 ml of anhydrous toluene for 20 hours at 100° C. The esterification mixture is worked up as described in Example 1(a).

9.34 g (=84% of theory) of the inverted formate are obtained after distillation.

Saponification of 8.80 g (40 mmol) of this formate with 0.4 ml of 30% strength sodium methoxide solution in 20 ml of methanol in accordance with Example 1(b), and distillation, gives 6.85 g (=89% of theory) of the inverted alcohol XII; boiling point: 125° C./0.1 mbar (S:R enantiomer ratio=31:69).

What is claimed is:

1. In the process for inverting the configuration of a secondary alcohol in which the hydroxyl group is attached to an asymmetric carbon atom, by esterification of this secondary alcohol with inversion of its configuration, and subsequent saponification of the ester with retention of the configuration of the secondary alcohol, the improvement comprising carrying out the esterification with inversion of the configuration by first converting the seoondary alcohol into an isourea ether and then reacting this isourea ether with a carboxylic acid to give the ester of the carboxylic acid.

2. The process oF claim 1, wherein the secondary alcohol is converted into the isourea ether by an addition reaction with a carbodiimide.

3. The process of claim 1, wherein the reaction of the isourea ether with the carboxylic acid is carried out in an aprotic solvent.

4. The process of claim 1, wherein a secondary alcohol of the formula

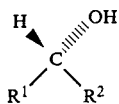

in which
R$^1$ and R$^2$ independently of one another are an optionally substituted, saturated or unsaturated, aliphatic or cycloaliphatic hydrocarbon radical or an optionally substituted araliphatic or aromatic hydrocarbon radical, or together form an asymmetric alkylene radical, subject to the proviso that R$^1$ is not identical with R$^2$,
is subjected to an addition reaction with a carbodiimide of the formula $$R^3-N=C=N-R^4$$

in which
R$^3$ and R$^4$ independently of one another are an alkyl, cycloalkyl, aralkyl or aryl radical,
and the resulting isourea ether of the formula

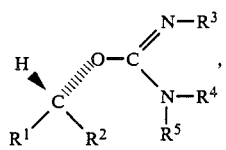

in which
R$^1$, R$^2$, R$^3$ and R$^4$ have the meaning indicated above and
R$^5$ is hydrogen
are reacted with a carboxylic acid of the formula $$R^6-CO_2H$$

in which
R$^6$ is hydrogen or an optionally substituted saturated or unsaturated aliphatic or cycloaliphatic hydrocarbon radical or an optionally substituted aromatic hydrocarbon radical,
with inversion of the configuration of the alcohol, to give an ester of the formula

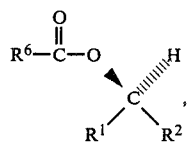

in which
R$^1$, R$^2$ and R$^6$ have the meaning mentioned above.

* * * * *